US00PP28347P3

(12) United States Plant Patent
Ranney

(10) Patent No.: US PP28,347 P3
(45) Date of Patent: Aug. 29, 2017

(54) ***DEUTZIA* PLANT NAMED 'NCDX2'**

(50) Latin Name: ***Deutzia* sp.**
Varietal Denomination: NCDX2

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 395 days.

(21) Appl. No.: 14/121,057

(22) Filed: Jul. 25, 2014

(65) Prior Publication Data

US 2016/0029530 P1 Jan. 28, 2016

(51) Int. Cl.
*A01H 5/02* (2006.01)

(52) U.S. Cl.
USPC ..... Plt./226

(58) Field of Classification Search
USPC ..... Plt./226
CPC ..... A01H 5/02; A01H 5/00
See application file for complete search history.

(56) References Cited

PUBLICATIONS

Flowering Shrubs, Spring Meadow Nursery, Inc. Starter Plants Catalog and Shrub Reference 2013-2014; Aug. 25, 2013, p. 34 (Yuki Cherry Blossom/*Deutzia* 'NCDX2').*

* cited by examiner

*Primary Examiner* — Kent L Bell
(74) *Attorney, Agent, or Firm* — Myers Bigel, P.A.

(57) ABSTRACT

'NCDX2' is a new cultivar of hybrid *Deutzia* with a compact, low-growing, arching/spreading growth habit with a profusion of showy pink-striped petals.

2 Drawing Sheets

Latin name of the genus and species: The Latin name of the novel plant variety disclosed herein is *Deutzia* sp.

Variety denomination: The inventive variety of *Deutzia* sp. disclosed herein has been given the varietal denomination 'NCDX2'.

BACKGROUND OF THE INVENTION

The present invention comprises a new and distinct cultivar of *Deutzia*, botanically known as *Deutzia* sp., and hereinafter referred to by the cultivar name 'NCDX2'. This new *Deutzia* was developed through a breeding program in Mills River, N.C. 'NCDX2' was selected from a population of seedlings grown from a controlled cross of *Deutzia gracillis* 'Nikko' NCSU 2005-118 (unpatented)×*Deutzia*×*rosea* 'Carminea' NCSU 2005-278 (unpatented) completed in April, 2009 and given the original experimental designation of H2010-310-034.

The first asexual propagation of 'NCDX2' was carried out in July 2011 by rooting stem cuttings in Mills River, N.C. and has been asexually reproduced repeatedly by vegetative cuttings over a 3 year period. 'NCDX2' roots readily from softwood cuttings treated with a basal dip of 2,000-5,000 ppm indole butyric acid (potassium salt) in water. 'NCDX2' has been found to retain its distinctive characteristics through successive asexual propagation of stem cuttings.

SUMMARY OF THE INVENTION

The following are the unique combination of characteristics of this new cultivar when grown under standard horticultural practices at North Carolina State University, Mountain Horticultural Crops Research Station, Mills River, N.C.:

1. Compact, low-growing, arching/spreading plant habit.
2. Prolific flowering.
3. Pink-striped petal color.

BRIEF DESCRIPTION OF THE DRAWINGS

This new *Deutzia* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *Deutzia*.

DETAILED BOTANICAL DESCRIPTION

Figure 1:
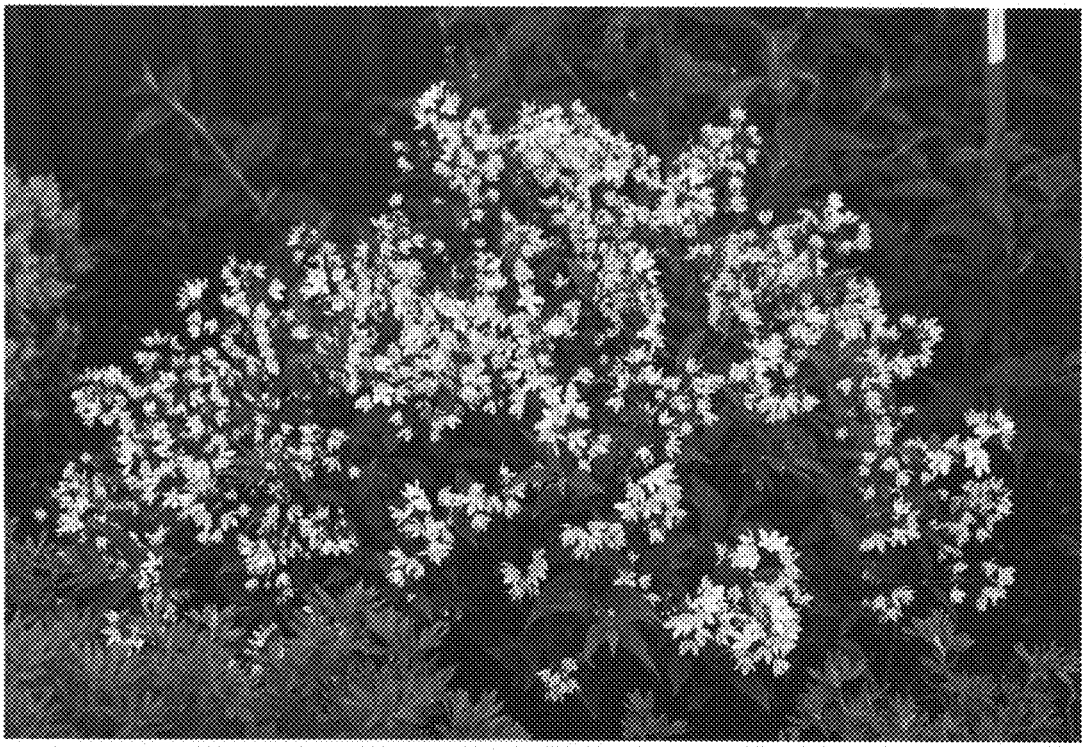
FIG. 1 is a color photograph showing the form and flowers of 'NCDX2' in spring 2013 on a two-year-old plant taken in Grand Haven, Mich.
Figure 2:
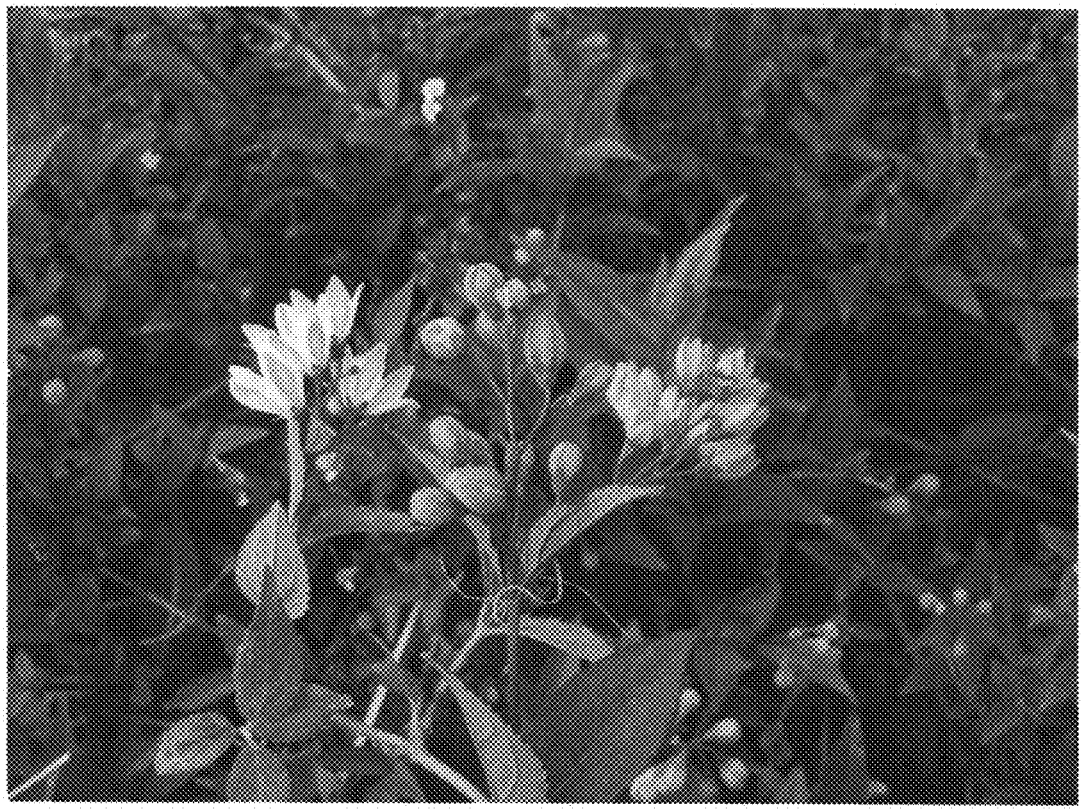
FIG. 2 is a color photograph of inflorescences of 'NCDX2' in spring 2013 on a two-year-old plant taken in Grand Haven, Mich.

The following is a detailed description of the botanical characteristics of the new and distinct hybrid *Deutzia* variety known by the denomination 'NCDX2'. The detailed description was taken on a three-year-old container-grown plant in Mills River, N.C. in 2013. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Deutzia* 'NCDX2'.

*Common name.*—*Deutzia.*

*Denomination.*—'NCDX2'.

Parentage:*Deutzia gracillis* 'Nikko' NCSU 2005-118 (not patented)×*Deutzia*×*rosea* 'Carminea' NCSU 2005-278 (not patented).

Plant description:

*Growth habit.*—Deciduous shrub. Compact, arching/spreading in shape.

*Height.*—About 24 cm. after 3 years.

*Width.*—About 80 cm. after 3 years.

Lateral branches:

*Number.*—Average 23 (typically ranging from 20-26).

*Length.*—Average 42 cm (typically ranging from 23-60 cm).

*Diameter.*—Average 3 mm (typically ranging from 2-5 mm).

*Strength.*—Medium.

*Color.*—Grey brown (RHS 199C).

*Texture.*—Glabrous with very few lenticels.

Shoot and stem:

*Immature shoot texture* (*current year*).—Glabrous.

*Immature shoot color* (*current year*).—Green (141C) to red-purple (59C).

*Mature stem texture* (*from prior year*).—Glabrous.

*Mature stem color* (*from prior year*).—Brown (N200B) to greyed red (178B).

Leaves:

*Length.*—Average 3.3 cm (typically ranging from 2.5-4.1 cm).

*Width.*—Average 1.3 cm (typically ranging from 0.7-1.9 cm).

*Type.*—Simple.

*Persistence.*—Deciduous.

*Arrangement.*—Opposite.

*Shape.*—Lanceolate.

*Apex.*—Acuminate.

*Base.*—Attenuate.

*Venation.*—Pinnate.

*Vein color.*—Green (147C) to red-purple (59C), upper and lower.

*Margins.*—Slightly serrate.

*Emerging leaves.*—Color: Upper: Green (143B). Lower: Green (143B). Texture: Upper surface scabrous; lower surface glabrous.

*Mature leaves during growing season.*—Color: Upper: Green (ranging from 139B to 139C) with a blush of red-purple (59C) including margins. Lower: Green (138C). Texture: Upper surface scabrous; lower surface glabrous.

*Petiole.*—Length: Avg. 4.7 mm, Range (3.9 to 5.4 mm). Diameter: Avg. 1 mm, Range (0.9 to 1.1 mm). Texture: Glabrous, upper and lower surface. Petiole color: Yellow-green (144B) to red-purple (59C), upper and lower surface.

Inflorescence:

*Description.*—Single, star-shaped flowers on terminal panicle.

*Height.*—6 cm.

*Diameter.*—5 cm.

*Number of true flowers per inflorescence.*—Avg. 10, Range (6 to 14).

*Number of flowers per lateral branch.*—Avg. 77.5, Range (42 to 113).

*Flowering season.*—Spring; Early to mid-May in Mills River, N.C.

*Lastingness of flower on the plant.*—3-4 weeks.

*Flower diameter.*—Avg. 16.6 mm, Range (10 to 23 mm).

*Flower depth.*—Avg. 12 mm, Range (9 to 15 mm).

*Flower self-cleaning or persistent.*—Self-cleaning, not persistent.

*Fragrance.*—Slight fragrance, sweet.

*Buds.*—Shape: Ovoid. Length: Avg. 6.6 mm, range (5.7 to 7.7 mm). Diameter: Avg. 3.2 mm, range (2.5 to 3.7 mm). Color: Red-purple (64C to 64D).

*Petals.*—Number: 5. Texture: Smooth, glabrous, both surfaces. Shape: Elliptic. Base: Attenuate. Margin: Entire. Apex: Obtuse to acute. Length: Avg. 12 mm, Range (10 to 13 mm). Width: Avg. 5 mm, Range (4 to 6 mm). Color when opening: Inner: White (155D). Outer: Bicolor with red-purple (64D) center stripe and white (155D) margin. Color at anthesis: Inner: White (155D). Outer: Bicolor with red-purple (64D to 79D) center striped and white (155D) margin.

*Calyx.*—Length/depth: Avg. 3.4 mm, range (2.5 to 4 mm). Diameter: Avg. 4.7 mm, range (4.2 to 5.7 mm).

*Sepal.*—Number: 6. Color, immature: Red-Purple (59C to 59D), inner and outer. Color, mature: Red-Purple (59C to 59D), inner and outer. Shape: Lanceolate. Texture: Smooth, glabrous, both surfaces. Length: Avg. 3.5 mm, range (3 to 4 mm). Width: Avg. 3.1 mm, range (2.3 to 3.4 mm). Apex: Acute. Margins: Entire.

*Peduncle.*—Length: Avg. 25 mm (20 to 30 mm). Width: Avg. 1.0 mm (0.8 to 1.2 mm). Color: Red-purple (59C). Texture: Smooth, glabrous.

*Pedicel.*—Length: Avg. 7.2 mm, range (5.4 to 8.7 mm). Diameter: Avg. 0.6 mm, range (0.4 to 0.7 mm). Color: Red-Purple (59C). Texture: Smooth, glabrous.

Reproductive organs:

*Gynoecium.*—Pistil number: 4. Pistil length: 5 mm. Stigma shape: Flattened, irregularly globoid. Stigma color: White (155D). Style length: 5 mm. Style color: White (155D). Ovary shape: Oval. Ovary color: Yellow-green (146A).

*Androecium.*—Stamen number: Avg. 9, Range (9 to 10). Anther shape: Round. Anther length: Less than 1 mm. Anther color: Yellow (12B). Pollen color: Yellow (12B). Pollen amount: Plentiful.

Disease and insect resistance: No significant disease or insect pests have been observed.

Cold hardiness: At least USDA zone 5; testing has not been completed in colder zones.

COMPARISON WITH COMMERCIAL CULTIVARS

Table 1 shows distinguishing characteristics between *Deutzia* 'NCDX2' and its parents. *Deutzia* 'NCDX2' is distinguished from *Deutzia* 'Nikko' in that 'NCDX2' has bicolor petals on the outer surface with pink centers (corresponding to red-purple (64D) in the R.H.S. colour chart) and white margins. 'NCDX2' is distinguished from *Deutzia×rosea* 'Carminea' by having a lower growth habit. 'NCDX2' also differs from other commercial cultivars. While *Deutzia* 'Duncan' (U.S. Plant Pat. No. 16,098) has yellow green (151D) foliage, *Deutzia* sp. 'NCDX2' foliage is green (ranging from 139B to 139C) with a blush of red-purple (59C). While *Deutzia* 'Kolmaspri' (U.S. Plant Pat. No. 20,964) has an upright habit and reaches 100 cm in height, *Deutzia* 'NCDX2' has an arched spreading form and reaches only 24 cm in height after three years. While *Deutzia* 'NCDX1' has white petals, *Deutzia* 'NCDX2' has bicolor petals on the outer surface with pink centers and white margins.

TABLE 1

Comparison of 'NCDX2' with parents.

| | Taxa | | |
|---|---|---|---|
| Trait | *Deutzia gracillis* 'Nikko' | *Deutzia* × *rosea* 'Carminea' | *Deutzia* 'NCDX2' |
| Plant height and diameter | 24 cm × 35 cm | 160 cm × 185 cm | 24 cm × 80 cm |
| Plant habit | Compact to rounded | Upright with arching branches | Compact, low growing |
| Flower diameter | Avg 11.1 mm (10.9 to 11.3 mm) | Avg. 14 mm (8.5 to 19.5 mm) | Avg. 16.6 mm (9.91 to 22.9 mm) |
| Fragrance | Slight | None | Slight |
| Petal color | White (155D), both surfaces | Inner: White (155D) Outer: Range, Red-Purple (63C) to White (155D) | Inner: White (155D) Outer: Range, Red-Purple (64D) to White (155D) |
| Flowers and flower buds per lateral branch | Avg 56.5 (38 to 75) | Avg 41 (27 to 55) | Avg 77.5 (42 to 113) |

What is claimed is:

1. A new and distinct hybrid *Deutzia* plant named 'NCDX2' substantially as illustrated and described herein.

* * * * *